US 6,589,903 B2

(12) United States Patent
Reitz et al.

(10) Patent No.: US 6,589,903 B2
(45) Date of Patent: Jul. 8, 2003

(54) METHOD OF SYNTHESIZING COMPLEXES OF PLATINUM AND ALKENYLPOLYSILOXANE, ESPECIALLY OF PLATINUM AND DIVINYLTETRAMETHYLDISILOXANE

(75) Inventors: Ramona Reitz, Biebergemünd (DE); Richard Walter, Alzenau (DE)

(73) Assignee: W. C. Heraeus GmbH & Co. KG, Hanau (DE)

( * ) Notice: Subject to any disclaimer, the term of this patent is extended or adjusted under 35 U.S.C. 154(b) by 0 days.

(21) Appl. No.: 09/910,494

(22) Filed: Jul. 19, 2001

(65) Prior Publication Data

US 2002/0099159 A1 Jul. 25, 2002

(30) Foreign Application Priority Data

Jul. 20, 2000 (DE) ......................... 100 35 644

(51) Int. Cl.$^7$ ................................ B01J 31/28
(52) U.S. Cl. .................. 502/158; 502/325; 528/15; 556/136; 556/9; 556/479
(58) Field of Search ................. 502/158, 325; 528/15; 556/136, 9, 479

(56) References Cited

U.S. PATENT DOCUMENTS

| 3,715,334 A | 2/1973 | Karstedt ................. 260/46.5 |
| 5,098,980 A | 3/1992 | Saruyama et al. ............ 528/15 |
| 5,175,325 A | * 12/1992 | Brown et al. |

FOREIGN PATENT DOCUMENTS

| EP | 0 894 804 A2 | 2/1999 | |
| EP | 0 979 837 A2 | 2/2000 | ......... C08G/77/398 |

* cited by examiner

Primary Examiner—Robert Dawson
Assistant Examiner—Kuo-Liang Peng
(74) Attorney, Agent, or Firm—Norris McLaughlin & Marcus

(57) ABSTRACT

A method for the synthesis of platinum alkenylpolysiloxane complexes, wherein a haloplatinum compound is reacted with at least one alkenylpolysiloxane, in the presence of a platinum complex as autocatalyst and a base, in an organic solvent.

16 Claims, No Drawings

METHOD OF SYNTHESIZING COMPLEXES OF PLATINUM AND ALKENYLPOLYSILOXANE, ESPECIALLY OF PLATINUM AND DIVINYLTETRAMETHYLDISILOXANE

The invention relates to a method for the synthesis of complexes of platinum and alkenylpolysiloxane, and especially to platinum divinyltetramethyldisiloxane, which is synthesized by this method, and to several uses.

In the EP 0 979 837 A2, a method is disclosed for the synthesis of a platinum hydrosilylation catalyst, for which initially a mixture of a haloplatinic acid, an alkenylpolysiloxane and a cycloalkylpolysiloxane is stirred at a particular temperature, after which the essentially the halogen is removed with sufficient alkali and the mixture is filtered, in order to obtain the corresponding platinum hydrosilylation catalyst. Moreover, 0.3 to about 20 moles of cycloalkylpolysiloxane per mole of alkenylpolysiloxane must be made available.

It is a disadvantage of this method that, for example, the platinum divinyltetramethyldisiloxane formed has a dark color, which does not meet the requirements (colorless to slightly yellow), which are required for certain specifications.

From the above, the problem arises of employing a novel method for synthesizing platinum alkenylpolysiloxane complexes or platinum divinyltetramethyldisiloxane, which eliminates the disadvantages named above at least partly, to make available especially a relatively inexpensive method for synthesizing the above compound, for which the platinum alkenylpolysiloxane complexes, especially the platinum divinyltetramethyldisiloxane, are almost colorless compounds.

This problem is solved by the method of the present invention. For the inventive method, initially a haloplatinum compound is reacted with at least one alkenylpolysiloxane with the addition of platinum in the form of a platinum complex as autocatalyst and with the addition of at least one base, especially of a hydrogen carbonate, carbonate or hydroxide, at the lowest possible temperature, especially at a temperature below +60° C., in an organic solvent mixture or solvent mixture, which can be oxidized by the haloplatinum compound.

As a rule, the reaction formulation is stirred during the reaction, for example, by means of a magnetic stirrer, for better mixing and in order to avoid local overheating. The individual reactants are added to the reaction formulation, for example, in portions or dropwise.

It was a surprising finding of essential importance to the invention that, upon adding small amounts of platinum alkenylpolysiloxane, the reaction, as such, is autocatalyzed so that the usual reaction temperature can be lowered by up to about 20° K. As a result, there is less decomposition and fewer byproducts are formed, so that the actual product is also contaminated less in color.

For a first variation of the inventive method, activated charcoal is added before the reaction. After the reaction, the activated charcoal suspension obtained is concentrated and, subsequently, the solid particles and activated charcoal are separated from a first liquid phase, preferably by filtration, or the solid particles and activated charcoal are separated from a first liquid phase and, subsequently, the first liquid phase is concentrated. The reaction product, a platinum alkenylpolysiloxane, is contained in the liquid phase.

In a second variation of the inventive method, the solid particles are separated from a first liquid phase after the reaction. Subsequently, the first liquid phase is treated with activated charcoal to form an activated charcoal suspension. After that, the suspension is concentrated and the activated charcoal is separated from the first liquid phase or the activated charcoal is separated from the first liquid phase and, subsequently, the first liquid phase is concentrated.

For a third variation of the inventive method, the reaction suspension obtained after the reaction is treated with activated charcoal to form an activated charcoal suspension. Subsequently, the activated charcoal suspension is concentrated, whereupon the solid particles and the activated charcoal are separated from a first liquid phase or the solid particles and activated charcoal are separated from a first liquid phase and, subsequently, the first liquid phase is concentrated.

It is of advantage if, for the reaction steps of the three alternative embodiments based on the platinum used as a haloplatinum compound, at least 1 percent by weight of platinum is used in the form of a platinum complex as autocatalyst.

Advantageously, the alkenylpolysiloxane is added first to the solvent or solvent mixture. This is followed by the addition of the haloplatinum compound. If the addition is reversed, unstable solutions may be formed, which may still react even days after they are formed.

For the inventive method, divinyltetramethyldisiloxane has proven its value in practice as alkenylpolysiloxane and hexachloroplatinic acid has proven its value in practice as haloplatinum compound.

Moreover, it has proven to be advantageous to wash the activated charcoal with the solvent or solvent mixture and to combine the second liquid phase obtained with the first liquid phase, in order to increase the yield of product.

Advantageously, it has proven to be of value in practice to use at least one alcohol, especially isopropanol and/or ethanol as solvent or solvent mixture.

If the haloplatinum compound is added as an anhydrous solution to the reaction formulation, especially as a solution of the haloplatinum compound in isopropanol, a controlled evolution of carbon dioxide gas takes place advantageously which, in turn, limits the discharge of the solvent by gas evolution, so that it is also possible to adhere to the strict emission limits.

Finally, it has proven to be advantageous in practice to carry out the reaction at a temperature of +42° C. to +58° C. and especially at a temperature of +48° C. to +52° C.

The alkenylpolysiloxane, especially the platinum divinyltetramethyldisiloxane, synthesized with this method, is almost colorless in comparison with the substances synthesized by methods known from the state of the art and has an iodine color number of 0 to 15 (measured according to DIN 6162).

Also of importance for the positive properties is the autocatalytic use of the actual product for synthesizing the same, since the reaction temperature can be lowered by up to about 20° K in this way, as a result of which fewer decomposition products and byproducts are formed and the reaction product is less contaminated.

The following examples explain the invention.

EXAMPLE 1

The synthesis is carried out under an inert gas.

Sodium hydrogen carbonate (42 g) is added to the apparatus and suspended in 62 ml of divinyltetramethyldisiloxane, 1 g of platinum siloxane con complex and 150 ml of isopropanol. The suspension is heated with stirring to a temperature of +48° C. to +52° C. and kept at this temperature.

A solution of 10 g of platinum as $H_2PtCl_6$ solid in 25 ml of isopropanol is prepared. Subsequently, the solution is run into the suspension in 5 ml steps, each subsequent addition being made after the suspension has decolorized once again. The temperature is maintained between +48° C. and +53° C.

The reaction is exothermic and a strong evolution of gas may be observed. The suspension is stirred for at least a further 2 hours, until it has decolorized. The suspension formed is cooled with stirring to room temperature and subsequently filtered through a G3 sintered glass disk. The filter cake is washed with 75 ml of isopropanol.

Subsequently, this solution ("solution 1") is treated with 6 g of activated charcoal and concentrated in a rotary evaporator under vacuum at a temperature not exceeding +45° C. (up to a platinum concentration of about 20%), until no further distillate is formed. The solution is then filtered through a Blauband filter.

The activated charcoal is washed with 200 ml of isopropanol and added to "solution 1" for the next experiment.

EXAMPLE 2

The synthesis is carried out under an inert gas.

Sodium hydrogen carbonate (42 g) is added to the apparatus and suspended with 69 g of trivinylpentamethyltrisiloxane, 2 g of platinum siloxane complex and 70 ml of ethanol. A solution of 10 g of platinum as $H_2PtCl_6$ solid in 25 m of ethanol is prepared. The further procedure is similar to that given in example 1. However, the reaction temperature is between 70° and 75° C. and ethanol is used to wash the filter cake and the activated charcoal.

EXAMPLE 3

The synthesis is carried out under an inert gas.

Sodium hydrogen carbonate (35 g) is added to the apparatus and suspended with 60 g of divinylhexamethyltrisiloxane, 2 g of platinum siloxane complex and 50 mL of ethanol. A solution of 10 g of platinum as $H_2PtCl_6$ solid in 25 m of ethanol is prepared. The further procedure is similar to that given in example 1. However, the reaction temperature is between +70° and +75° C. and ethanol is used to wash the filter cake and the activated charcoal.

EXAMPLE 4

The synthesis is carried out under an inert gas.

Sodium hydrogen carbonate (37 g) is added to the apparatus and suspended with 77 g of divinyldiphenyldimethyldisiloxane, 2 g of platinum siloxane complex and 50 mL of ethanol. A solution of 10 g of platinum as $H_2PtCl_6$ solid in 25 m of ethanol is prepared. The further procedure is similar to that given in example 1. However, the reaction temperature is between +70° and +75° C. and ethanol is used to wash the filter cake and the activated charcoal.

What is claimed is:

1. A method for the synthesis of platinum alkenylpolysiloxane complexes, comprising the steps of:
    a1.) reacting a haloplatinum compound with a suspension of at least one alkenylpolysiloxane, a platinum complex as autocatalyst, at least one base, and activated charcoal, in a liquid comprised of an organic solvent or solvent mixture which is oxidizable by the haloplatinum compound;
    b1.) concentrating the suspension and subsequently separating the suspension into a solid phase and a liquid phase or separating the suspension into a solid phase and a liquid phase and subsequently concentrating the liquid phase; or
    a2.) reacting a haloplatinum compound with a suspension of at least one alkenylpolysiloxane, a platinum complex as autocatalyst, and at least one base, in a liquid comprised of an organic solvent or solvent mixture which is oxidizable by the haloplatinum compound;
    b2.) separating the suspension into a solid phase and a liquid phase and subsequently treating the liquid phase with activated charcoal to form a suspension of activated charcoal;
    c2.) concentrating the suspension of activated charcoal and subsequently separating the activated charcoal from the liquid phase or separating the activated charcoal from the liquid phase and subsequently concentrating the liquid phase; or
    a3.) reacting a haloplatinum compound with a suspension of at least one alkenylpolysiloxane, a platinum complex as autocatalyst, and at least one base, in an organic solvent or solvent mixture which is oxidizable by the haloplatinum compound;
    b3.) treating the suspension with activated charcoal;
    c3.) concentrating the suspension and subsequently separating the suspension into a solid phase and a liquid phase and subsequently concentrating the liquid phase.

2. The method of claim 1, wherein platinum, in the form of a platinum complex, is used as autocatalyst in steps a1.), a2.) and a3.) in an amount of at least 1% in relation to the platinum used as haloplatinum compound.

3. The method of claim 1 or 2, wherein initially the alkenylpolysiloxane is added to the solvent or solvent mixture and subsequently the haloplatinum compound is added thereto.

4. The method of claim 1 or 2 wherein the alkenylpolysiloxane is divinyltetramethyldisiloxane.

5. The method of claim 1 or 2, wherein the haloplatinum compound is hexachloroplatinic acid.

6. The method of claim 1 or 2, wherein the separated solid phase is washed with a solvent or mixture of solvents and then the solvent or mixture of solvents used to wash the separated solid phase is recovered and added to the liquid phase.

7. The method of claim 1 or 2, wherein at least one alcohol is used as solvent or mixture of solvents.

8. The method of claim 7, wherein the alcohol used is isopropanol, ethanol or a mixture thereof.

9. The method of claim 1 or 2, wherein the haloplatinum compound is added to the reaction formulation as an anhydrous solution.

10. The method of claim 9, wherein a solution of a haloplatinum compound in isopropanol is used.

11. The method of claim 1 or 2, wherein the reaction is carried out at a temperature of +42° to +58° C.

12. The method of claim 11, wherein the reaction is carried out at a temperature of +48° to +52° C.

13. A method for catalyzing the synthesis of platinum alkenylpolysiloxane, which comprises catalyzing said synthesis with a platinum alkenylpolysiloxane as autocatalyst.

14. A method for catalyzing the synthesis of platinum divinyltetramethyldisiloxane which comprises catalyzing said synthesis with platinum divinyltetramethyldisiloxane as autocatalyst.

15. The method of claim 1 or 2 wherein said autocatalyst is platinum alkenylpolysiloxane.

16. The method of claim 1 or 2 wherein said autocatalyst is platinum divinyltetramethyldisiloxane.

* * * * *